US006486205B2

(12) United States Patent
Gonzáles Bravo et al.

(10) Patent No.: US 6,486,205 B2
(45) Date of Patent: *Nov. 26, 2002

(54) MIXTURE OF PRIMARY FATTY ACIDS OBTAINED FROM SUGAR CANE WAX

(75) Inventors: Luis Gonzáles Bravo; David Marrero Delange; Abilo Laguna Granja; Rosa Maria Más Ferreiro; Maria de Lourdes Arruzazabala Valmana; Daysi Carbajal Quintana; Mirian Cora Medina; Roberto Menendez Soto del Valle, all of Habana (CU)

(73) Assignee: Laboratorios Dalmer SA, Habana (CU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 114 days.

(21) Appl. No.: 09/402,292

(22) PCT Filed: Apr. 1, 1998

(86) PCT No.: PCT/IB98/00870
§ 371 (c)(1),
(2), (4) Date: Jan. 19, 2000

(87) PCT Pub. No.: WO98/43631
PCT Pub. Date: Oct. 8, 1998

(65) Prior Publication Data
US 2002/0058705 A1 May 16, 2002

(30) Foreign Application Priority Data
Apr. 2, 1997 (CU) ................................................. 35/97

(51) Int. Cl.[7] .......................... A61K 31/20; A61K 9/20; A23L 1/28
(52) U.S. Cl. ....................... 514/558; 424/464; 426/425; 426/429; 426/431; 426/472; 426/478; 426/655; 514/822; 514/925; 514/960
(58) Field of Search ................................. 514/553, 557, 514/558, 560, 822, 925, 960; 424/464; 426/425, 429, 431, 472, 478, 655

(56) References Cited

U.S. PATENT DOCUMENTS

| 5,243,094 A | * | 9/1993 | Borg | ........................... 568/822 |
| 5,554,379 A | * | 9/1996 | Cuca et al. | .................. 424/439 |
| 6,039,950 A | * | 3/2000 | Kwaia et al. | ............. 424/195.1 |
| 6,080,787 A | * | 6/2000 | Carlson et al. | ............. 514/560 |

FOREIGN PATENT DOCUMENTS

WO    WO 94/07830    *    4/1994

OTHER PUBLICATIONS

WO 9845390 A (1998), Abstract . . .*
JP 7-011284 A (1995), Abstract . . .*
JP 6200289 A (1994), Abstract.*
JP 6-200288 A (1994), Abstract.*
JP 6-200287 A (1994), Abstract.*
JP 6-122892 A (1994), Abstract.*
STN/CAS online, file CAPLUS, Acc. No. 1972:485628, Doc. No. 77:85628, (Flores et al., Acta Cient. Venez. (1971), vol. 22, No. 5, pp. 147,148), Abstract.*
Hornstra, "Effect of dietary lipids on arterial thrombus formation: rationale for the support of drug therapy by diet," Semin. Thromb. Hemostasis (1988), 14(1), pp 59–65.*
Toyota et al., "Studies of Brazilian crude drugs. 1. Muira–puama." Shoyakugaku Zasshi (1979), 33(2), pp 57–64.*

* cited by examiner

Primary Examiner—Allen J. Robinson
Assistant Examiner—Frank Choi
(74) Attorney, Agent, or Firm—Lorusso & Loud

(57) ABSTRACT

A new natural mixture of primary fatty acids of high molecular weight ranging from 24 to 38 carbon atoms, especially those ranging between 26 and 36 carbon atoms and more especially those of straight chain of 26, 28, 29, 30, 31, 32, 33, 34, 35 and 36 carbon atoms. This mixture has a relative composition of each fatty acid that is highly reproducible batch to batch and it is extracted from sugar cane (*Saccharum officinarum,* L.) wax. This mixture of fatty acids has specific pharmacological properties that supports its use as an active component of pharmaceutical formulations used as hypocholesterolemic and against hypercholesterolaemia type II, as antiplatelet, anti-thrombotic and anti-ischemic. This mixture of primary fatty acids is also effective in the inhibition of the development of gastric ulcers induced by different agents.

19 Claims, No Drawings

MIXTURE OF PRIMARY FATTY ACIDS OBTAINED FROM SUGAR CANE WAX

This application is a 371 of PCT/IB98/00780 filed Apr. 1, 1998.

This invention relates to a new mixture of primary fatty acids with straight chains of 26, 28, 29, 30, 31, 32, 33, 34, 35 and 36 carbon atoms. This mixture shows a relative composition of the fatty acids that is highly reproducible from batch to batch and it is extracted from sugar cane (Saccharum officinarum L.) wax, and can be used for the treatment of type II hypercholesterolemia, as antiplatelet agent, as anti-thrombotic, as anti-ischemic agent as well as protective and/or curative agent against gastric ulcers.

There are other mixtures of fatty acids that has reported biological properties, such is the case of the one reported in U.S. Pat. No. 5,284,873 in which is claimed a pharmaceutical composition for combatting prostate affections, in which the active principle is a fraction of fatty acids obtained from the fruits of Sabal Serrulata, with oleic acid as the main one, followed by lauric and palmitic acids, being the one with the greater number of carbon atom eicosenoic. In the U.S. Pat. No. 5,502,045 is claimed a method of reducing the cholesterol levels in serum using an ester formed by a-sitostanol and a 2 fatty acid from 2 to 22 carbon atoms. Also, claims a method of formation of such esters, being the effective daily dose of 0.2 to 20 g of the ester. Although, in the U.S. Pat. No. 5,444,054 is reported a method of treating ulcerative colitis in which one of the fractions used is an oil that contains certain fatty acids from 18 to 22 carbon atoms, but unsaturated. Not close to this patent application are the U.S. Pat. Nos. 4,505,933 and 4,687,783 in which are claimed mixtures of fatty aldehydes derived from fatty acids, for the treatment of patients with multiple sclerosis as well as neurological and dermatological diseases, the inventors claims a daily dose of 100–400 mg/kg of body weight of the patients.

In the last decade, numerous patent have appeared which report the omega-3-poly-unsaturated fatty acids have an effect on serum cholesterol and blood platelet aggregation, such is the case of U.S. Pat. No. 4,526,902 where it is claimed a pharmaceutical composition for the treatment of thrombo-embolic conditions in which the active principle are unsaturated eicosapentaenoic and docohexacnoic fatty acids together with linoleic acid, linolenic acid and its derivatives. Also, in the U.S. Pat. No. 5,502,077 is claimed a composition of fatty acids for the treatment or prophylaxis of multiple risk factors for cardiovascular diseases, where the 80% in weight corresponds with omega-3 fatty acids, its salts or derivatives thereof, being the main ones eicosapentaenoic and docohcxacnoic acids. In EPO patent 0 422 490 A2 it is claimed a pharmaceutical composition for inhibiting the absorption of cholesterol, containing triglycerides formed, preferably, by a mixture of saturated fatty acids from 20 to 24 carbon atoms, but they should be administered in a daily dose of 2 to 10 g. Also, in the Japanese patents 55092316 A and 56115736 A. of Tokiwa Shizeru et al, is reported the demonstration as well as the isolation and purification of an agent for diminishing cholesterol composed by a mixture of highly unsaturated fatty acids, especially eicosatrienoic and docosatertraenoicacids. In other Japanese patents (publication # 1290625 A, 02053724 A, 02243622 A and 04169524 A) claimed different pharmaceutical formulations, such as an improver of cerebral function or for the treatment of degenerative disease, or for lowering cholesterol in blood and for having Serum lipid-improving activity in which are presents as active principle, mixtures of fatty acids, especially eicosapentaenoic and docosahexacnoic acids, in a daily dose that varies from 500 mg/kg of body weight to 0.5–30 g.

As it has been shown, these patents claims mixture of fatty acid with specific biological properties, some of them closely related with the ones claimed in the present patent application. But, the composition of these mixtures significantly differs from the one claimed in these patent application and, also, the proposed daily dose to be used in these treatments in higher than the one claimed in the present patent application.

The present invention is related mainly with the pharmaceutical industry, particularly with the development of pharmaceutical formulations with specific properties, because them could be used as hypocholesterolaemic and hypolypoproteinaemic, anti-platelet anti-thrombotic, anti-ischemic drugs as well as in the prevention of gastric and duodenal ulcers induced by different agents.

These formulations contains, as active principle, a natural mixture of primary fatty acids of high molecular weight ranging from 24 to 38 carbon atoms, especially those ranging from 26 to 36 carbon atoms and more especially those of straight chain of 26, 28,29,30,31,32,33,34,35 and 36 carbon atoms, obtained from sugar cane wax (named MFASCW).

Drugs with specific pharmacological properties, based in the uses of primary fatty acids of high molecular weight (from 26 to 36 carbon atoms) obtained from, vegetable or animal waxes as active principles has not been reported previously, but it is known that primary fatty alcohols of high molecular weight obtained from sugar cave wax shows the same pharmacological properties. In EPO patent 0 488 928 A2 is claimed a mixture of fatty alcohols of high molecular weight for the treatment of hypercholesterolaemia and hyperlypoproteinaemia, type II that., also, in patent WO 94/07830 is claimed the use of the same mixture as anti-platelet agent, anti-ischemic, anti-thrombotic as well as in the prevention of gastric and duodenal ulcers induced by different agents.

The procedure for the obtention of this mixture of primary fatty acids of high molecular weight in the present invention is based in an homogeneous saponification of sugar cane wax with concentrated solutions of alkaline and earth-alkaline hydroxides, especially those of low molecular weight and more especially those of sodium, potassium and calcium. The concentration of the alkaline solution must be such that the ratio in weight of the corresponding hydroxide with that of the wax to be processed must be over 5% on, especially from 8 to 25% and more specifically from 15 to 25%. Saponification process lasts for a period over 30 min and more especially between 1 to 5 hours. The solid, obtained in this step, is processed using a conventional solid-liquid extractor, where the M.F.A.S.C.W., in salt form, is isolated from the rest of the components by extracting these components using the adequate organic solvent choose among ketones from 3 to 8 carbon atoms, alcohols from 1 to 5 carbon atoms, hydrocarbons from 5 to 8 carbon atoms, haloforms as well as aromatic compounds including mixtures of them. Some preferred solvents used in the present invention are the following: acetone, methyl-ethyl ketone, pentanone, hexanone, terbutanol, ethanol, methanol, 2-propanol, butanol, hexane, pentane, isopentane, ciclohexane, heptane, chloroform, 1,2 dichloroethane, dichloromethane, trichloroethane, trichloromethane, 1,2,3 trichloropropane, benzene, toluene, phenol, p-methyl toluene and others.

The mixture of primary fatty acids of high molecular weight in salt form is purified by succesive recristalizations in an adequate organic solvents or in aqueous solutions, choosen among ketones from 3 to 8 carbon atoms, alcohols from 1 to 5 carbon atoms, hydrocarbons from 5 to 8 carbon atoms, as well as aromatic compounds, including mixtures of them. Some preferred solvents used in this step of the process acetone, methyl-ethyl ketone, pentanone, hexanone, terbutanol, ethanol, methanol, 2-propanol, butanol, hexane, pentane, heptane, octane, ciclohexane, benzene, toluene, phenol, p-methyl toluene and water between others.

An step in the purification of this mixture of primary fatty acids of high molecular weight consist in refluxing the components in an adequate organic solvent, choose among ketones from 3 to 8 carbon atoms, alcohols from 1 to 5 carbon atoms, hydrocarbons from 5 to 8 carbon atoms as well as aromatic compounds including mixtures of them and, immediately, hot filtering the fatty acids salts.

In the final step of this process the free fatty acids are regenerated using an acid solution, that could be prepared using mineral acids and/or organic acids to be choose among hydrochloric acid, sulphuric acid, nitric acid, perchloric acid, acetic acid and oxalic acid among others. The yield of fatty acid is between 10 to 40%, while the purity of the M.F.A.S.C.W. is in the general range from 85 to 100%, more especially between 90 to 99%, determined using gas chromatography and/or volumetric chemical analysis.

The M.F.A.S.C.W. obtained in the present invention is a mixture of primary fatty acids of high molecular weight ranging from 26 to 36 carbon atoms, more especially the one of 26, 28, 29, 30, 31, 32, 33, 34, 35 and 36 carbon atoms. In Table I is reported the qualitative and quantitative composition of this M.F.A.S.C.W.

TABLE I

Qualitative and quantitative composition of the M.F.A.S.C.W.

| Component | Percent in the mixture (%) |
| --- | --- |
| 1-hexacosanoic | 0.3–1.5 |
| 1-octacosanoic | 25.0–50.0 |
| 1-nonacosanoic | 1.0–3.0 |
| 1-triacontanoic | 15.0–30.0 |
| 1-hentriacontanoic | 0.8–3.0 |
| 1-dotriacontanoic | 10.0–22.0 |
| 1-tritriacontanoic | 1.0–3.0 |
| 1-tetratriacontanoic | 10.0–22.0 |
| 1-pentatriacontanoic | 0.5–1.5 |
| 1-hexatriacontanoic | 2.0–9.0 |

The daily dose of M.F.A.S.C.W. to be used for the treatment of the different diseases has been established between 1 to 100 mg per day and the most adequate route of administration is oral solid dosage-form such as tablets, gragees or capsules. Also, this drug could be administered orally or parenterally or topically considering the uses claimed in the present invention.

The pharmaceutical formulation, used in the oral route contains as active principle from 0.5 to 25.0% in weight of M.F.A.S.C.W. This dose is obtained by mixing M.F.A.S.C.W. with different excipients such as disintegrators, agglutinants, lubricants, sliders or just fillers.

One of the objects of the present invention is to isolate and purify the natural mixture of primary fatty acis with high molecular weight ranging from 26 to 36 carbon atoms from sugar cane wax, especially the mixture of straight chain fatty acids of 26, 28, 29, 30, 31, 32, 33, 34, 35 and 36 carbon atoms.

Other of the objects of this invention is to use this natural mixture of fatty acids, in relatively low doses, as a component of pharmaceutical formulations used as hypocholesterolemic and hypolipidaemic drugs. Also, one of the objects of the present invention is the development of pharmaceutical formulations that contains M.F.A.S.C.W. as active principle in order to be used as anti-ischemic and anti-thrombotic drugs, administered orally, topically or parenterally.

Finally, in a whole picture of M.F.A.S.C.W. profile, and proposed as active principle for pharmaceutical formulations, this mixture is innocuos, and very well tolerated, representing an important advantage. Thus, results obtained in toxicological assays carried out in rodents report absence of toxicity related with the M.F.A.S.C.W.. No side effects have been detected in subjects treated with the product which is object of the present invention. The object of the current invention shall be described in detail in the following pages. References will be made to examples of accomplishments that are not limited to the scope of the said invention.

EXAMPLE 1

One thousand (1000) g of refined sugar cane wax were taken and melted at 100–110° C. and 200 g of potassium hydroxide are added dissolved in 150 mL of water. The saponification process is maintained for 30 min with stirring periodically. The fatty acid is extracted from the solid obtained in the process using acetone in a solid-liquid extraction system. The obtained residue is cooled to room temperature, recrystallized in heptane and, later on, is refluxed with methanol for 2 h, with a final hot filtration. M.F.A.S.C.W. is regenerated by treatment with concentrate sulphuric acid. 250 g of this M.F.A.S.C.W. were obtained with a purity amounting to 94.0%.

EXAMPLE 2

Ten (10) kg of refined sugar cane wax were taken and melted at 100–110° C. to which 2 kg of sodium hydroxide dissolved in 1.5 L of water was added. The hydrolisis process is maintained for a period of two hours, stirring periodically. The solid obtainec in the process is extracted with ethanol in a conventional solid-liquid extraction system. The extract obtained was cooled to room temperature, the solid obtained was recrystallized in acetone and, later on, is refluxed for two hours in pentane, with a final hot filtration. M.F.A.S.C.W. was obtained by treatment of the solid with concentrate nitric acid and 2.45 kg of M.F.A.S.C.W. were aobtained with a purity amounting 95.0%.

EXAMPLE 3

Ten (10) kg of raw sugar cane wax were taken and melted adding 2.5 kg of calcium hydroxide dissolved in water. The saponification process was maintained for 30 min, with periodically stirring. The solid obtained in the process was extracted with acetone in a solid-liquid extraction system. The residue obtained in this step of the process was cooled to room temperature, recrystallized in benzene and, later on, refluxed for one hour in toluene for a final hot filtration. M.F.A.S.C.W. was obtained by treatment of the solid with concentrate sulphuric acid. 2.3 kg of M.F.A.S.C.W. were obtained with a purity amounting 93.5%.

EXAMPLE 4

Fifty (50) kg of refined sugar cane wax were taken and melted and enough quantity of potassium hydroxide dissolved in water were added. The saponification process was maintained for 30 min stirring periodically. The solid obtained in the process was extracted with chloroform in a solid-liquid extraction system. The residue obtained in this step of the process was cooled at room temperature and recrystallized in methyl ethyl ketone. Later on, it was refluxed for 3 hours in methanol for a final hot filtration. M.F.A.S.C.W. was obtained by treatment of the solid with concentrate hydrochloric acid. 13.6 kg of M.F.A.S.C.W. were obtained with a purity amounting 96.0%

EXAMPLE 5

One thousand (1000) g of refined sugar cane wax were taken to be melted at 100–110° C. adding 250 g of potassium hydroxide dissolved in 250 mL of water and the wax was saponified for 1 hour with periodically stirring. The solid obtained in the process was extracted with n-hexane in a solid-liquid extraction system for 12 h. The residue obtained in this step of the process was cooled at room temperature, recrystallized in ethanol and, later on, refluxed in acetone for 30 min with a final hot filtration. M.F.A.S.C.W. was regenerated by treatment with an aqueous solution of sulphuric acid. Two hundreds (250) g of M.F.A.S.C.W. were obtained with a purity amounting 96.7%.

EXAMPLE 6

Two different pharmaceutical formulations, tablets type, using M.F.A.S.C.W. as active principle, are developed. The composition of these pharmaceutical formulations are presented in Table II. These formulations were developed considering the physical, chemical and chemical-physical characteristics of the active principle.

TABLE II

Pharmaceutical formulations tablets type using M.F.A.S.C.W. as active principle

| Component | Formulation 1 (%) | Formulation 2 (%) |
| --- | --- | --- |
| M.F.A.S.C.W. | 5.0 | 15.0 |
| Lactose | 56.5 | 55.0 |
| Corn starch | 15.0 | 10.0 |
| Gelatin | 2.5 | 2.0 |
| Sodium croscarmellose | 5.0 | 4.0 |
| Talc | 2.0 | 2.0 |
| Magnesium stearate | 1.5 | 1.0 |
| Mycrocrystalline cellulose | 7.5 | 7.0 |

EXAMPLE 7

The object of this work is to evaluate the effect of M.F.A.S.C.W. on the platelet aggregation induced in rats. A group of male Sprague Dawley weighing 250 to 300 g were adapted to laboratory conditions (25+/31 2° C., ligth/darkness cycles of 12 h) with free access to water and food for 15 days. M.F.A.S.C.W. was prepared as a suspension in an Acacia gum/water vehicle (10 mg/mL) and orally administered by gastric gavage. Animals were randomly distributed among three experimental groups: 1) controls, animals receiving vehicle in an equivalent volume; 2) animals receiving M.F.A.S.C.W. 20 mg/kg and 3) animals receiving M.F.A.S.C.W. 200 mg/kg. All animals were deprived of food for 12 h prior to the administration of the drug. To conduct the assay, rats were anaesthetized with sodium pentobarbital and 30 min after the administration of the drug, the abdomens were opened and blood was drawn from the vein cava mixed with sodium citrate (1 voluime of citrate per 9 of blood). Platelet-rich plasma (PRP) was obtained by blood centrifugation for 10 min at 160 g. Platelet-poor plasma (PPP) was obtained by centrifugation of plama aliquots for 5 min at 2500 g. Platelet aggregation was determined according to the Born method, using an Elvi −840 aggregometer at 37° C. and stirring (1000 rpm). Platelet aggregation levels were measured after calibrating the equipment at 0% light transmission for PRP and at 100% for PPP. ADP (Sigma) was used for inducing platelet aggregation.

The statistical comparison of results between treatment and control groups was carried out using the nonparametric Mann-Whitney U Test.

The M.F.A.S.C.W. (20 and 200 mg/kg) administered in unique doses showed a significant inhibition of platelet aggregation induced by ADP in rats, as is shown in Table III. These results corroborate the M.F.A.S.C.W. acts as an antiplatelet drug.

TABLE III

Effect of M.F.A.S.C.W. on platelet aggregation in rats

| Treatment | Dose (mg)kg) | n | 5 mM ADP % of platelet aggregation (values are the mean ± SD) |
| --- | --- | --- | --- |
| Control |  | 12 | 39.5 ± 12.6 |
| M.F.A.S.C.W. | 20 | 6 | 24.2 ± 7.5* |
| M.F.A.S.C.W. | 200 mg/kg | 5 | 19.8 ± 4.3** |

* $p < 0.05$; **$p < 0.01$ Comparison with controls. (Mann-Whitney U test).

EXAMPLE 8

In this study were investigated the effects of M.F.A.S.C.W. on veinous thrombosis experimentally induced in rats and its possible effects on the bleeding time. Male Sprague Dawley rats weighing 300 to 350 g were adapted to laboratory conditions (25±2° C., ligth/darkness cycles of 12 h) with free access to water and food for 7 days. M.F.A.S.C.W. was orally administered (5 mg/kg body weight) by gastric gavage as a suspension in an Acacia gum-water vehicle (10 mg/mL). Animals were randomly distributed in three experimental groups: 1) controls only receiving vehicle; 2) M.F.A.S.C.W. 5 mg/kg body weight and 3) M.F.A.S.C.W. 100 mg/kg body weight. One hour after the administration of the substances, rats were anaesthetized using sodium pentobarbital (30 mg/kg) and the tail of the animals was submerged in a saline solution at 37° C., two (2) cm of the last portion of this tail were cutted and the bleeding time was measured using a digital chronometer.

Veinous thrombosis: Animals were randomly distributed in four experimental groups 1) controls; 2, 3 and 4 receiving M.F.A.S.C.W. at doses of 20, 100 and 200 mg/kg respectively.

Induction of thrombosis: All the treatments were administered orally and after an hour the animals were anaesthetized using sodium pentobarbital injected intraperitoneal route with hypotonic saline solution (0.22%) (1 ml/100 g of body weight), immediately their abdomens were opened and the cava vein was ligated in its upper part (2 cm) and part of this vein was collected in a filter paper and opened, extracting the thrombo that was transferred to a Petri's dishes with a filter paper humected in physiological saline solution standing at room temperature for an hour. This weight of the thrombo weas determined after that time.

The statistical comparison of results between treatment and control groups was carried out using the nonparametric Mann-Whitney U Test and for the analysis of the incidence was used the Fisher's Test.

Orally administered M.F.A.S.C.W. at dose of 100 mg/kg and 200 mg/kg significatively orevent veinous thrombosis but not the dose of 20 mg/kg. The results are shown in Table IV and V.

TABLE IV

Effect of M.F.A.S.C.W. over veinous thrombosis in rats (x ± SD)

| Treatment | Dose (mg/kg) | n | Thrombo weight (mg) | Incidence of thrombos (%) |
|---|---|---|---|---|
| Control | — | 20 | 4.12 ± 2.7 | 69 |
| M.F.A.S.C.W. | 20 | 11 | 5.24 ± 4.4 | 73.4 |
| M.F.A.S.C.W | 100 | 9 | 3.24 ± 3.2* | 64.3 |
| M.F.A.S.C.W | 200 | 11 | 2.40 ± 1.3* | 48 |

*$p < 0.05$ Mann-Whitney U Test

TABLE V

Effect of M.F.A.S.C.W. on the bleeding time of rats

| Treatment | Dose (mg/kg) | n | Bleeding time (s) | |
|---|---|---|---|---|
| Control | — | 15 | 215.8 ± 10.4 | |
| M.F.A.S.C.W. | 25 | 15 | 230.6 ± 25.5 | ns |
| M.F.A.S.C.W. | 100 | 13 | 249.0 ± 14.8 | ns | ns: non significative.

As can be observed, the results demonstrated that M.F.A.S.C.W., in the range of doses assayed, diminished the size and weight of the thrombo in rats without increasing the bleeding time. These results demonstrated that M.F.A.S.C.W. shows anti-thrombotic effects without provoquing significative changes in blood coagulation, representing an advantage to diminish the effects of bleeding in the anti-thrombotic therapy and suggest that the mechanism of action could be related with an effect over the platelet rather than an inhibition of coagulation factors, between others.

EXAMPLE 9

To analyze the effect of the M.F.A.S.C.W. on experimentally induced gastric ulcers were studied two experimental models, in one the gastric ulcer is induced by ethanol and in the other by stress. Male and female Sprague Dawley rats weighing 200 to 250 g were adapted to laboratory conditions (25±2° C., ligth/darkness cycles of 12 h) with free access to water and food for 7 days. M.F.A.S.C.W. was prepared as a suspension in an Acacia gum/water vehicle. Animals were randomly distributed in different experimental groups and the administration of products was orally done using a gastric gavage (5 ml/kg body weight), the controls only received equivalent volumes of the vehicle. According to the experimental series the induction of gastric ulcer was induced by oral administration of ethanol (60%) or by stress. After a 24 hours fast period, gastric ulcers were induced in the animals.

Induction with ethanol: rats were randomly distributed in 4 experimental groups: 1) control and 2, 3 and 4) treated with M.F.A.S.C.W. at 25, 50 and 100 mg/kg respectively. An hour after treatment, each rat was administered 1 mL of ethanol by gastric gavage. One hour later, rats were sacrificed, their stomach were immediately removed, opened lengthwise along the greater curvature and washed with distilled water, then the damaged area was measured by means of a magnifying glass (×3).

Induction by stress: Animals were randomly distributed in three (3) experimental groups: 1) controls and 2 and 3 M.F.A.S.C.W. 50 and 200 mg/kg respectively. Immediately after treatment rats were individually immobilized in 5 cm diameter iron cylinders and submerged in a water bath at 24±1° C. up to the xyfoid level in order to produce stress in the rats. Animals were sacrificed 7 hours later, the stomachs were immediately removed, opened lengthwise along the greater curvature and washed with distilled water. The damaged areas were measured by two independent specialist in a double blind fashion. Lesions were evaluated as the total sumatory of the sizes of the damaged areas reported as mm of gastric ulcers.

All comparison between treatment and control groups were performed using the nonparametric Mann-Whitney U Test.

As is observed in Table VI, M.F.A.S.C.W. (100 mg/kg) significantly inhibited the occurence of gastric ulcers induced by ethanol.

TABLE VI

Effect of M.F.A.S.C.W. on gastric ulcers induced by ethanol (60%)

| Treatment | Dose (mg/kg) | n | Ulcer size (mm) | Inhibition % |
|---|---|---|---|---|
| Control | — | 13 | 16.2 ± 5.8 | — |
| M.F.A.S.C.W. | 25 | 10 | 10.9 ± 2.9 | 19 |
| M.F.A.S.C.W. | 50 | 9 | 8.4 ± 2.7 | 40 |
| M.F.A.S.C.W. | 100 | 10 | 5.0 ± 2.2* | 64 |

*$p < 0.05$ (Mann-Whitney U Test)

In Table IV are shown the results of M.F.A.S.C.W. on gastric ulcers indiced by stress.

TABLE VII

Effect of M.F.A.S.C.W. on the gastric ulcers induced by stress (inmovilization and inmersion)

| Treatment | Dose (mg/kg) | n | Ulcer's size (mm) |
|---|---|---|---|
| Control | — | 14 | 46.1 ± 3.5 |
| M.F.A.S.C.W. | 50 | 6 | 44.9 ± 7.9 |
| M.F.A.S.C.W. | 200 | 6 | 26.8 ± 5.1** |

*$p \ll 0.05$, **$p \ll 0.01$ Mann-Whitney U Test

As can be appreciated, M.F.A.S.C.W. protect the gastric mucose from lesions induced both by ethanol or by stress, being a model independent of the administered dose example 10.

Tablets containing 5 mg of M.F.A.S.C.W. were administered to a groups of patients affected with hypercholesteroleamia type II. Before these patients were included in the study, they suffered a 4 weeks of diet only period and only those having LDL-C values higher than 3.8 mmol/L were included in the study. Treatment with M.F.A.S.C.W. was maintained for 6 weeks. During this active treatment period, dietary conditions were maintained. After that period, the lipid profile was determined to each patient, results are reported in Tables VIII and IX.

TABLE VIII

Effect of MFASCW 5 mg on cholesterol and triglycerides serum levels

| | Cholesterol (mmol/L) | | Triglycerides (mmol/L) | |
|---|---|---|---|---|
| | Weeks | | | |
| Patient | 0 | 6 | 0 | 6 |
| 1 | 6.46 | 6.05 | 2.15 | 2.04 |
| 2 | 6.40 | 5.41 | 2.77 | 2.04 |
| 3 | 7.48 | 6.17 | 1.71 | 2.10 |

TABLE VIII-continued

Effect of MFASCW 5 mg on cholesterol and triglycerides serum levels

| | Cholesterol (mmol/L) | | Triglycerides (mmol/L) | |
|---|---|---|---|---|
| | Weeks | | | |
| Patient | 0 | 6 | 0 | 6 |
| 4 | 10.71 | 7.48 | 2.26 | 2.25 |
| 5 | 7.62 | 6.80 | 3.81 | 3.04 |
| 6 | 6.33 | 5.29 | 1.81 | 1.71 |
| 7 | 7.32 | 6.31 | 1.73 | 1.61 |
| 8 | 7.76 | 6.86 | 2.20 | 1.70 |
| 9 | 7.80 | 6.99 | 4.30 | 3.50 |
| 10 | 7.00 | 5.20 | 2.30 | 1.60 |
| 11 | 6.86 | 5.45 | 2.90 | 2.70 |
| 12 | 7.21 | 6.00 | 1.80 | 1.20 |
| 13 | 6.40 | 5.00 | 3.30 | 1.80 |
| 14 | 6.90 | 5.80 | 2.20 | 2.00 |
| 15 | 8.35 | 6.78 | 4.00 | 3.20 |
| 16 | 6.40 | 5.10 | 1.20 | 0.80 |
| 17 | 9.20 | 6.35 | 2.80 | 1.70 |
| 18 | 6.58 | 5.00 | 1.90 | 1.35 |
| 19 | 6.85 | — | 2.00 | — |
| $\overline{X}$ | 7.35 | 6.00 | 2.44 | 2.05 |
| Δ% | | 18.2% | | 17.4% |

TABLE IX

Effect of M.F.A.S.C.W. 5 mg on serum low density lipoproteins (LDL-C) as well as high density lipoproteins (HDL-C)

| | LDL-C (mmol/L) | | HDL-C (mmol/L) | |
|---|---|---|---|---|
| | Weeks | | | |
| Patient | 0 | 6 | 0 | 6 |
| 1 | 5.25 | 5.02 | 1.00 | 1.60 |
| 2 | 4.91 | 4.92 | 0.85 | 1.20 |
| 3 | 6.77 | 6.20 | 1.50 | 1.61 |
| 4 | 8.45 | 9.01 | 1.35 | 1.40 |
| 5 | 3.48 | — | 0.75 | 1.20 |
| 6 | 9.95 | 8.85 | 1.12 | 1.08 |
| 7 | 7.70 | — | 1.01 | 1.10 |
| 8 | 4.42 | 4.27 | 0.90 | 1.30 |
| 9 | 4.72 | 5.24 | — | — |
| 10 | 6.18 | 4.64 | — | — |
| 11 | 5.47 | 5.34 | 0.88 | 0.98 |
| 12 | 4.04 | 3.66 | 1.15 | 1.20 |
| 13 | 5.25 | 5.04 | 1.89 | 1.65 |
| 14 | 6.31 | 4.33 | 1.05 | 1.56 |
| 15 | 4.78 | 4.25 | 0.68 | 0.85 |
| 16 | 5.51 | 5.16 | 1.30 | 1.20 |
| 17 | 5.40 | 5.02 | 1.12 | 1.60 |
| 18 | 5.60 | 4.96 | 0.98 | 0.96 |
| 19 | 5.20 | — | 0.78 | — |
| X | 5.40 | 3.98 | 1.08 | 1.28 |
| Δ% | | 25.4% | | 20.7% |

It can be observed that, after a 6 weeks treatment period, is produced a significative reduction of cholesterol ($p<0.001$), triglycerides ($p<0.01$) and LDL-C levels ($p<0.001$), as well as an significative increase ($p<0.05$) of HDL-C levels. The average reductions were of 18.2% (cholesterol), 17.4% (triglycerides), 25.7% (LDL-C) and the increase of HDL-C was of 20.7%.

These results demonstrate that treatment with M.F.A.S.C.W. is very effective, because in the 100% of the patients the final levels were lower than that of the beginning of the treatment and the variation percentages are bigger that the limits required by a drug to be considered as effective in the reduction of cholesterol and LDL-C.

What is claimed is:
1. A pharmaceutically beneficial composition of primary fatty acids consisting of a mixture of:
    (a) 1-hexacosanoic acid;
    (b) 1-octacosanoic acid;
    (c) 1-nonacosanoic acid;
    (d) 1-triacontanoic acid;
    (e) 1-hentriacontanoic acid;
    (f) 1-dotriacontanoic acid;
    (g) 1-tritriacontanoic acid;
    (h) 1-tetratriacontanoic acid;
    (i) 1-pentatriacontanoic acid; and,
    (j) 1-hexatriacontanoic acid;
wherein said pharmaceutically beneficial composition of primary fatty acids are a natural mixture obtained from a homogeneous saponification of sugar cane wax and substantially free of other fatty acids having 24 to 38 carbon atoms.

2. A pharmaceutically beneficial composition of primary fatty acids wherein said mixture comprises:
    (a) 1-hexacosanoic acid which is about 0.3 to 1.5% of total weight;
    (b) 1-octacosanoic acid which is about 25 to 50% of total weight;
    (c) 1-nonacosanoic acid which is about 1 to 3% of total weight;
    (d) 1-triacontanoic acid which is about 15 to 30% of total weight;
    (e) 1-hentriacontanoic acid which is about 0.8 to 3% of total weight;
    (f) 1-dotriacontanoic acid which is about 10 to 22% of total weight;
    (g) 1-tritriacontanoic acid which is about 1 to 3% of total weight;
    (h) 1-tetratriacontanoic acid which is about 10 to 22% of total weight;
    (i) 1-pentatriacontanoic acid which is about 0.5 to 1.5% of total weight; and,
    (j) 1-hexatriacontanoic acid which is about 2 to 9% of total weight wherein said pharmaceutically beneficial composition of primary fatty acids is a natural mixture obtained from a homogeneous saponification of sugar cane.

3. The pharmaceutically beneficial composition of primary fatty acids according to claim 2 wherein said composition further comprises:
    an oral delivery device wherein said device is selected from the group consisting of tablets, dragees, and capsules wherein said mixture comprises about 0.5 to 25% by weight of said oral delivery device; and,
    a delivery aid wherein said delivery aid is an acceptable pharmaceutical excipient wherein said delivery aid comprises the remaining percentage of total weight of said oral delivery device.

4. The pharmaceutically beneficial composition of primary fatty acids according to claim 3 wherein said acceptable pharmaceutical excipients are selected from the group consisting of fillers, agglutinants, disintegrators, lubricants, and sliders.

5. The pharmaceutically beneficial composition of primary fatty acids according to claim 3 wherein said oral delivery device is a tablet further comprising a mixture of lactose, corn starch, gelatin, sodium croscarmellose, talc, magnesium stearate and microcrystalline cellulose.

6. A method of treating medical conditions comprising the steps of:
diagnosing whether a medical condition exists which is treatable with primary fatty acids wherein said medical condition is selected from a group consisting of type II hypercholesterolemia, ischemia, thrombosis, platelet aggregation and gastric ulcers induced by compounds, agents or drugs; and,
administering a therapeutically beneficial dosage of a composition of primary fatty acids comprising a mixture of:
(a) 1-hexacosanoic acid;
(b) 1-octacosanoic acid;
(c) 1-nonacosanoic acid;
(d) 1-triacontanoic acid;
(e) 1-hentriacontanoic acid;
(f) 1-dotriacontanoic acid;
(g) 1-tritriacontanoic acid;
(h) 1-tetratriacontanoic acid;
(i) 1-pentatriacontanoic acid; and,
(j) 1-hexatriacontanoic acid
wherein said therapeutically beneficial dosage of a composition of primary fatty acids is a natural mixture obtained from a homogeneous saponification of sugar cane.

7. The method according to claim 6 wherein said medical condition is selected from a group consisting of type II hypercholesterolemia, ischemia, thrombosis, and platelet aggregation.

8. The method according to claim 7 wherein said therapeutically beneficial dosage of primary fatty acids is about 1 to about 100 mg daily.

9. The method according to claim 8 wherein said therapeutically beneficial dosage of primary fatty acids is administered orally or parenterally and is about 10 to 20 mg daily.

10. A method for obtaining a pharmaceutically beneficial composition of primary fatty acids mixture as free acids or in form of their salt from sugar cane wax comprising the steps of:
saponifying sugar cane wax with a concentrated hydroxide solution for at least 30 minutes wherein said concentrated hydroxide solution is selected from the group consisting of alkalines and earth alkalines;
isolating said fatty acid mixture from the rest of the components of said homogeneous saponification of sugar cane wax by extracting said components from said saponified wax using a solid-liquid extraction system, wherein said solid-liquid extraction system uses an extraction solvent wherein said extraction solvents are selected from the group consisting of ketones having 3 to 8 carbon atoms, alcohols having 1 to 5 carbon atoms, hydrocarbons having 5 to 8 carbon atoms, haloforms, aromatic compounds, mixtures and aqueous solutions thereof;
purifying the mixture by successive recrystallizations wherein successive recrystallizations are preformed in a recrystallization solution wherein said recrystallization solution is selected from the group consisting of ketones having 3 to 8 carbon atoms, alcohols having 1 to 5 carbon atoms, hydrocarbons having 5 to 8 carbon atoms, aromatic compounds, mixtures thereof, aqueous solutions thereof and water;
refluxing the components in an adequate reflux solvent wherein said reflux solvents are selected from the group consisting of ketones having 3 to 8 carbon atoms, alcohols having 1 to 5 carbon atoms, hydrocarbons having 5 to 8 carbon atoms, aromatic compounds, mixtures and aqueous solutions thereof;
hot filtering immediately thereafter the mixture; and,
regenerating the mixture using a regeneration solution wherein said regeneration solution is selected from the group consisting of organic acids, mineral acids, and combinations thereof wherein the regeneration produces the mixture comprising:
(a) 1-hexacosanoic acid;
(b) 1-octacosanoic acid;
(c) 1-nonacosanoic acid;
(d) 1-triacontanoic acid;
(e) 1-hentriacontanoic acid;
(f) 1-dotriacontanoic acid;
(g) 1-tritriacontanoic acid;
(h) 1-tetratriacontanoic acid;
(i) 1-pentatriacontanoic acid; and,
(j) 1-hexatriacontanoic acid.

11. The method according to claim 10:
wherein said concentrated hydroxide solution has a hydroxide weight of at least 5% to 25% of that of the weight of the wax to be processed;
wherein said saponification lasts for a period of at least 30 minutes and up to 5 hours;
wherein said extraction of said mixture ranges from 1 to 20 hours;
wherein said recrystallization ranges from 15 minutes up to 3 hours; and,
wherein said refluxing is performed between 15 minutes and 3 hours.

12. The method according to claim 8 wherein said concentrated hydroxide solution is selected from the group consisting of sodium, potassium and calcium.

13. The method according to claim 10 wherein said successive recrystallizations are preformed in a recrystallization solution which is selected from the group consisting of, methanol, ethanol, n-propanol, 2-propanol, n-butanol, n-pentanol, terbutanol, mixtures and aqueous solutions thereof;
wherein said extraction solvents are selected from the group consisting of methanol, ethanol, n-propanol, 2-propanol, n-butanol, n-pentanol, terbutanol, mixtures and aqueous solutions thereof;
wherein said reflux solvents are selected from the group consisting of methanol, ethanol, n-propanol, 2-propanol, n-butanol, n-pentanol, terbutanol, mixtures and aqueous solutions thereof.

14. The method according to claim 10 wherein said recrystallization solvent is selected from the group consisting of benzene, toluene, ethyl benzene, phenol, p-methyl toluene and mixtures thereof;
wherein said extraction solvent is selected from the group consisting of benzene, toluene, ethyl benzene, phenol p-methyl toluene and mixtures thereof;
wherein said reflux solvent which is selected from the group consisting of benzene, toluene, ethyl benzene, phenol p-methyl toluene and mixtures thereof.

15. The method according to claim 10 wherein said extraction solvent which is selected from the group consisting of chloroform, 1,2-dichloroethane, dichloromethane, trichloroethane, trichloromethane, 1,2,3-trichloropropane, and mixtures thereof.

16. The method according to claim 10 wherein said recrystallization solution is selected from the group consisting of hexane, pentane, isopentane, cyclohexane, heptane and mixtures thereof;
wherein said extraction solvent is selected from the group consisting of hexane, pentane, isopentane, cyclohexane, heptane and mixtures thereof;

wherein said reflux solvent is selected from the group consisting of hexane, pentane, isopentane, cyclohexane, heptane and mixtures thereof.

17. The method according to claim 10 wherein said recrystallization solution is water.

18. The method according to claim 10 wherein said regeneration solution is selected from the group consisting of hydrochloric acid, sulfuric acid, nitric acid, perchloric acid, acetic acid, oxalic acid and combinations thereof.

19. The method according to claim 10:

wherein said recrystallization solution is selected from the group consisting of acetone, methyl butyl ketone, pentanone, methyl ethyl ketone, hexanone, mixtures thereof and aqueous solutions thereof;

wherein said extraction solution is selected from the group consisting of acetone, methyl butyl ketone, pentanone, methyl ethyl ketone, hexanone, and mixtures thereof;

wherein said reflux solvent is selected from the group consisting of acetone, methyl butyl ketone, pentanone, methyl ethyl ketone, hexanone and mixtures thereof.

* * * * *

UNITED STATES PATENT AND TRADEMARK OFFICE
CERTIFICATE OF CORRECTION

PATENT NO. : 6,486,205 B2
DATED : November 26, 2002
INVENTOR(S) : Gonzales Bravo et al.

It is certified that error appears in the above-identified patent and that said Letters Patent is hereby corrected as shown below:

<u>Column 5,</u>
Line 52, delete "(25+/31" and insert -- (25+/- --

<u>Column 6,</u>
Line 42, delete "5mg/kg" and insert -- 25 mg/kg --

<u>Column 12,</u>
Lines 28-31, delete claim 12 and insert claim 12 as follows:
-- 12. The method according to claim 10 wherein said concentrated hydroxide solution is selected from the group consisting of sodium, potassium and calcium. --

Signed and Sealed this

Twenty-seventh Day of May, 2003

JAMES E. ROGAN
*Director of the United States Patent and Trademark Office*